US012690799B2

(12) United States Patent
Jang et al.

(10) Patent No.: US 12,690,799 B2
(45) Date of Patent: Jul. 28, 2026

(54) METHOD, SYSTEM AND NON-TRANSITORY COMPUTER- READABLE RECORDING MEDIUM FOR DETECTING AND CLASSIFYING BEAT IN ELECTROCARDIOGRAM SIGNAL

(71) Applicant: HUINNO, Co., Ltd., Seoul (KR)

(72) Inventors: Jae Seong Jang, Seoul (KR); Seong Jae Park, Namyangju-si (KR); Jin Guk Kim, Seoul (KR); Jun Ho An, Seoul (KR); Sung Hoon Jung, Seoul (KR)

(73) Assignee: HUINNO, Co., Ltd., Seoul (KR)

( * ) Notice: Subject to any disclaimer, the term of this patent is extended or adjusted under 35 U.S.C. 154(b) by 394 days.

(21) Appl. No.: 18/347,309

(22) Filed: Jul. 5, 2023

(65) Prior Publication Data

US 2024/0016434 A1 Jan. 18, 2024

(30) Foreign Application Priority Data

Jul. 8, 2022 (KR) ........................ 10-2022-0084605

(51) Int. Cl.
| | |
|---|---|
| *A61B 5/00* | (2006.01) |
| *A61B 5/352* | (2021.01) |
| *A61B 5/366* | (2021.01) |

(52) U.S. Cl.
CPC .............. *A61B 5/366* (2021.01); *A61B 5/352* (2021.01); *A61B 5/7282* (2013.01)

(58) Field of Classification Search
CPC ....... A61B 5/366; A61B 5/352; A61B 5/7282; A61B 5/349; A61B 5/7235–7267
See application file for complete search history.

(56) References Cited

U.S. PATENT DOCUMENTS

| | | | |
|---|---|---|---|
| 2018/0249964 A1* | 9/2018 | Qian | .................... A61B 5/0245 |
| 2020/0260980 A1* | 8/2020 | Liu | ........................ A61B 5/316 |

* cited by examiner

*Primary Examiner* — Scott M. Getzow
(74) *Attorney, Agent, or Firm* — United One Law Group LLC; Kongsik Kim; Jhongwoo Peck

(57) ABSTRACT
A method for detecting and classifying a beat in an electro-cardiogram (ECG) signal includes detecting a QRS wave-form in an ECG signal using a waveform detection model, and detecting a class of a cardiac event capable of being derived from the QRS waveform; and detecting a unique R-peak in the QRS waveform using a regression model.

9 Claims, 6 Drawing Sheets

200

METHOD, SYSTEM AND NON-TRANSITORY COMPUTER- READABLE RECORDING MEDIUM FOR DETECTING AND CLASSIFYING BEAT IN ELECTROCARDIOGRAM SIGNAL

CROSS-REFERENCE TO RELATED APPLICATION

The present application claims priority from Korean Application No. 10-2022-0084605 filed Jul. 8, 2022, which is incorporated herein by reference in its entirety.

TECHNICAL FIELD

The present invention relates to a method, system, and non-transitory computer-readable recording medium for detecting and classifying a beat in an electrocardiogram (ECG) signal.

RELATED ART

Recently, methods using convolutional neural network (CNN)-based semantic segmentation have been proposed to detect and classify beats in electrocardiogram (ECG) signals.

The proposed methods detect sections such as P-wave, QRS complex, and T-wave, which are characteristic of ECG signals, through segmentation.

Here, an R-peak in a QRS waveform is determined as a single point, and thus when the location of the R-peak is to be determined by segmentation alone, there is a possibility that multiple R-peaks are detected in a single QRS waveform or an R-peak is detected outside of the QRS waveform.

Therefore, there is a limitation in using only a CNN-based semantic segmentation model to detect a beat and its R-peak in an ECG signal, and additional processing of the output of the CNN-based model is required to detect a unique R-peak in a single QRS waveform.

SUMMARY

One object of the present invention is to solve all the above-described problems in prior art.

Another object of the invention is to accurately detect a QRS waveform in an ECG signal.

Yet another object of the invention is to accurately classify to which class a QRS waveform detected in an ECG signal belongs.

Still another object of the invention is to detect a unique R-peak in a QRS waveform detected in an ECG signal.

The representative configurations of the invention to achieve the above objects are described below.

According to one aspect of the invention, there is provided a method for detecting and classifying a beat in an electrocardiogram (ECG) signal, the method comprising the steps of: detecting a QRS waveform in an ECG signal using a waveform detection model, and detecting a class of a cardiac event capable of being derived from the QRS waveform; and detecting a unique R-peak in the QRS waveform using a regression model.

According to another aspect of the invention, there is provided a system for detecting and classifying a beat in an ECG signal, the system comprising: a first detection unit configured to detect a QRS waveform in an ECG signal using a waveform detection model, and detect a class of a cardiac event capable of being derived from the QRS waveform; and a second detection unit configured to detect a unique R-peak in the QRS waveform using a regression model.

In addition, there are further provided other methods and systems to implement the invention, as well as non-transitory computer-readable recording media having stored thereon computer programs for executing the methods.

According to the invention, it is possible to accurately detect a QRS waveform in an ECG signal.

According to the invention, it is possible to accurately classify to which class a QRS waveform detected in an ECG signal belongs.

According to the invention, it is possible to detect a unique R-peak in a QRS waveform detected in an ECG signal.

DETAILED DESCRIPTION

Figure 1:
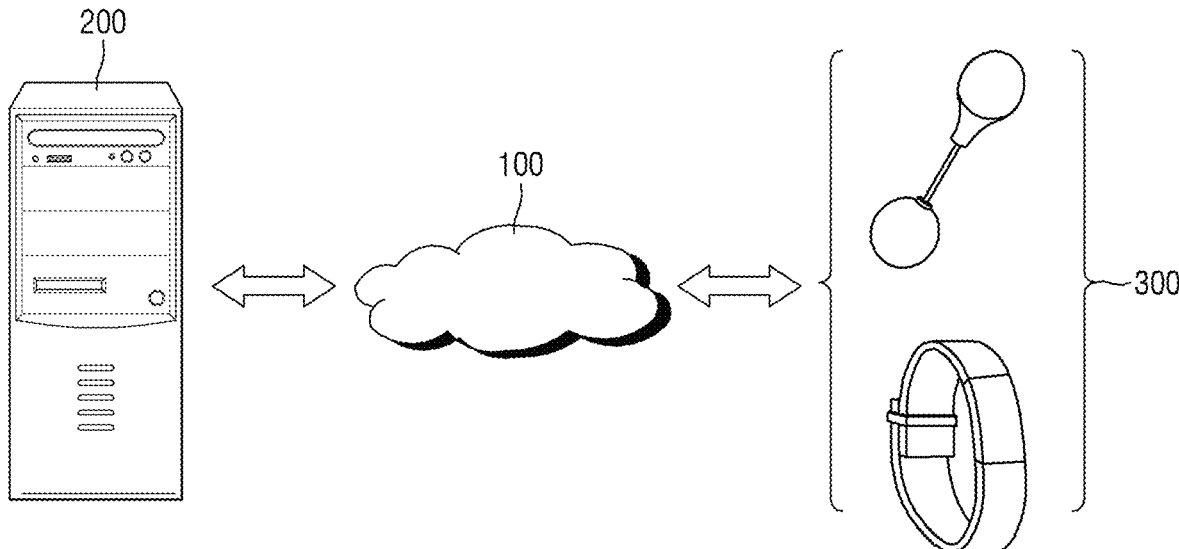
FIG. 1 schematically shows the configuration of an entire system for detecting and classifying a beat in an electrocardiogram (ECG) signal according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, and characteristics described herein may be implemented as modified from one embodiment to another without departing from the spirit and scope of the invention. Furthermore, it shall be understood that the positions or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of the Entire System

FIG. 1 schematically shows the configuration of the entire system for detecting and classifying a beat in an electrocardiogram (ECG) signal according to one embodiment of the invention.

As shown in FIG. 1, the entire system according to one embodiment of the invention may comprise a communication network 100, an ECG signal processing system 200, and a device 300.

First, the communication network 100 according to one embodiment of the invention may be implemented regardless of communication modality such as wired and wireless communications, and may be constructed from a variety of communication networks such as local area networks (LANs), metropolitan area networks (MANs), and wide area networks (WANs). Preferably, the communication network 100 described herein may be the Internet or the World Wide Web (WWW). However, the communication network 100 is not necessarily limited thereto, and may at least partially include known wired/wireless data communication networks, known telephone networks, or known wired/wireless television communication networks.

For example, the communication network 100 may be a wireless data communication network, at least a part of which may be implemented with a conventional communication scheme such as WiFi communication, WiFi-Direct communication, Long Term Evolution (LTE) communication, 5G communication, Bluetooth communication (including Bluetooth Low Energy (BLE) communication), infrared communication, and ultrasonic communication. As another example, the communication network 100 may be an optical communication network, at least a part of which may be implemented with a conventional communication scheme such as LiFi (Light Fidelity).

Next, the ECG signal processing system 200 according to one embodiment of the invention may communicate with the device 300 to be described below via the communication network 100. Further, the ECG signal processing system 200 according to one embodiment of the invention may function to detect a QRS waveform in an ECG signal using a waveform detection model, and detect a class of a cardiac event capable of being derived from the QRS waveform, and to detect a unique R-peak in the QRS waveform using a regression model. Meanwhile, the ECG signal processing system 200 may be digital equipment having a memory means and a microprocessor for computing capabilities, and may be, for example, a server system operating on the communication network 100.

The configuration and functions of the ECG signal processing system 200 according to one embodiment of the invention will be discussed in detail below.

Next, the device 300 according to one embodiment of the invention is digital equipment capable of connecting to and then communicating with the ECG signal processing system 200, and having a memory means and a microprocessor for computing capabilities, such as a smart patch, a smart watch, a smart band, and smart glasses, and may be a wearable monitoring device including a sensing means (e.g., a contact electrode) for measuring a biosignal (e.g., an ECG signal) from a human body, and a display means for providing a user with a variety of information on the measurement of the biosignal.

Further, according to one embodiment of the invention, the device 300 may further include an application program for performing the functions according to the invention. The application may reside in the device 300 in the form of a program module. The characteristics of the program module may be generally similar to those of a first detection unit 210, a second detection unit 220, a communication unit 230, and a control unit 240 of the ECG signal processing system 200 to be described below. Here, at least a part of the application may be replaced with a hardware device or a firmware device that may perform a substantially equal or equivalent function, as necessary.

Configuration of the ECG Signal Processing System

Hereinafter, the internal configuration of the ECG signal processing system 200 crucial for implementing the invention and the functions of the respective components thereof will be discussed.

Figure 2:
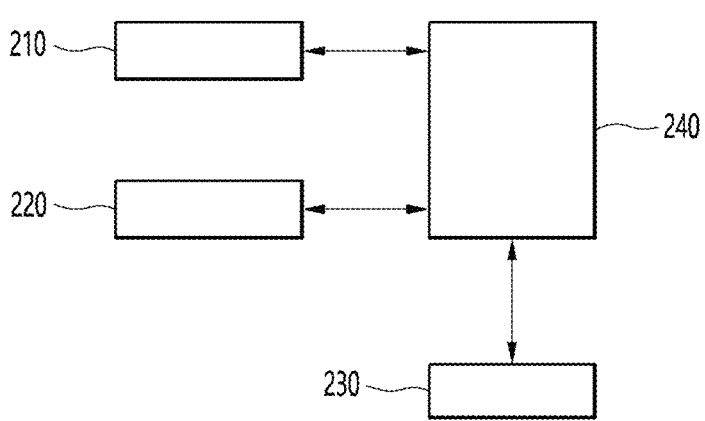
FIG. 2 specifically shows the internal configuration of an ECG signal processing system according to one embodiment of the invention.

FIG. 2 specifically shows the internal configuration of the ECG signal processing system 200 according to one embodiment of the invention.

As shown in FIG. 2, the ECG signal processing system 200 according to one embodiment of the invention may comprise a first detection unit 210, a second detection unit 220, a communication unit 230, and a control unit 240. According to one embodiment of the invention, at least some of the first detection unit 210, the second detection unit 220, the communication unit 230, and the control unit 240 may be program modules to communicate with an external system (not shown). The program modules may be included in the ECG signal processing system 200 in the form of operating systems, application program modules, or other program modules, while they may be physically stored in a variety of commonly known storage devices. Further, the program modules may also be stored in a remote storage device that may communicate with the ECG signal processing system 200. Meanwhile, such program modules may include, but are not limited to, routines, subroutines, programs, objects, components, data structures, and the like for performing specific tasks or executing specific abstract data types as will be described below in accordance with the invention.

Meanwhile, the above description is illustrative although the ECG signal processing system 200 has been described as above, and it will be apparent to those skilled in the art that at least a part of the components or functions of the ECG signal processing system 200 may be implemented in the device 300 or a server (not shown) or included in an external system (not shown), as necessary.

First, the first detection unit 210 according to one embodiment of the invention may function to detect a QRS waveform in an ECG signal using a waveform detection model.

Here, the waveform detection model according to one embodiment of the invention is a convolutional neural network (CNN)-based model for performing semantic segmentation on the ECG signal, and may be a general CNN-based model (specifically, a typical U-Net model) that further includes residual blocks and squeeze-and-excitation (SE) blocks.

Figure 3:
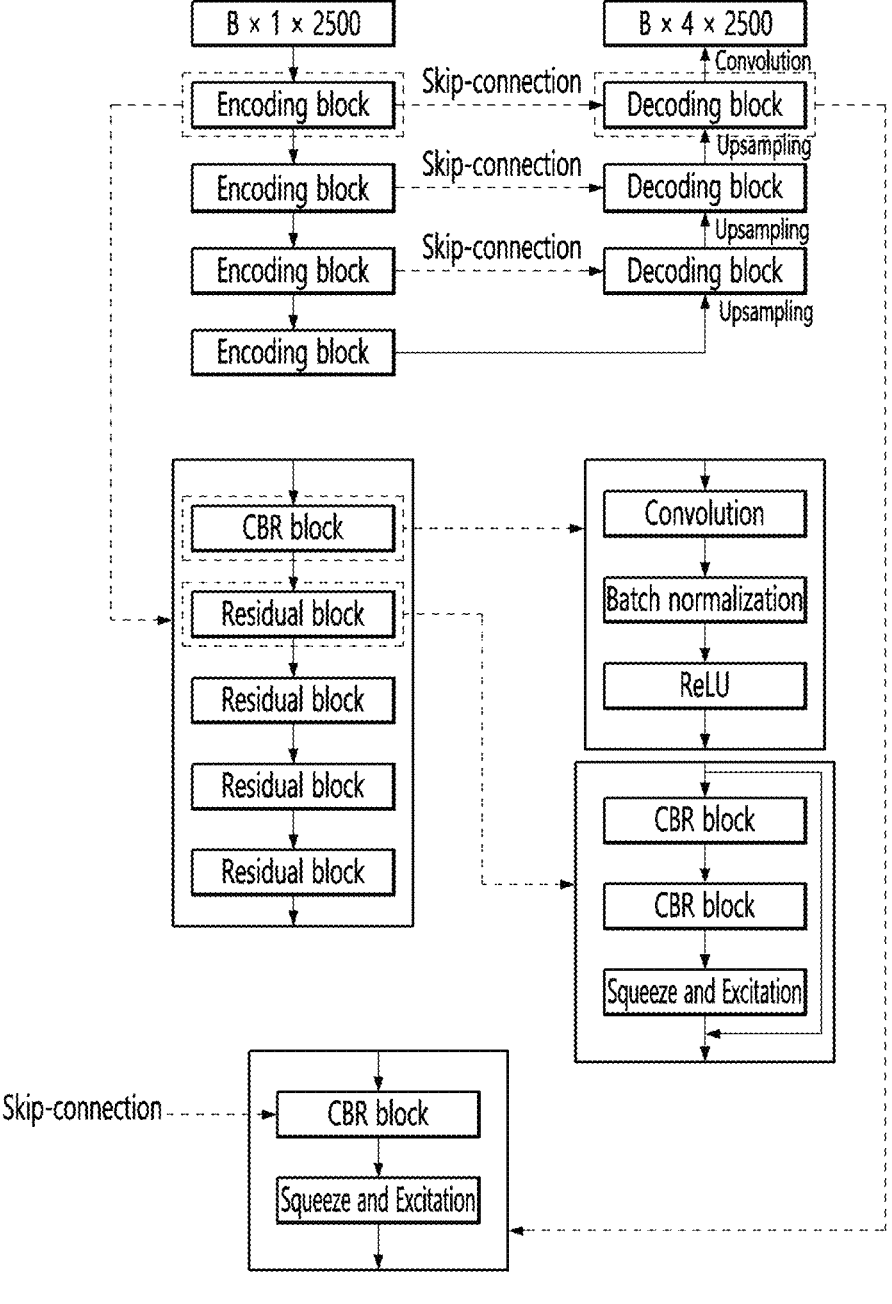
FIG. 3 shows the structure of a waveform detection model according to one embodiment of the invention.

Specifically, referring to FIG. 3, the waveform detection model according to one embodiment of the invention may be formed in a structure in which a plurality of encoding blocks (specifically, four encoding blocks) and a plurality of decoding blocks (specifically, three decoding blocks) are successively connected like a typical U-Net model. However, unlike the typical U-Net model, the waveform detection model according to one embodiment of the invention may be formed in a structure in which the encoding blocks may include a single CBR block and a plurality of residual blocks (specifically, four residual blocks) (whereas the encoding blocks in the typical U-Net model consist of only CBR blocks), and the plurality of residual blocks are successively connected at the end of the single CBR block. Further, unlike the typical U-Net model, the waveform detection model according to one embodiment of the invention may be formed in a structure in which the decoding blocks may include a single CBR block and a single SE block (whereas the decoding blocks in the typical U-Net model consist of only CBR blocks), and the single SE block is successively connected at the end of the single CBR block. Here, according to one embodiment of the invention, a CBR block may refer to a sequential arrangement of a convolution layer, a batch normalization layer, and an ReLU activation function. Further, according to one embodiment of the invention, a residual block may refer to a successive connection of a plurality of CBR blocks (specifically, two CBR blocks) and a single SE block (i.e., according to one embodiment of the invention, each of the plurality of residual blocks may include an SE block). As such, unlike the typical U-Net model, the waveform detection model according to one embodiment of the invention may further include residual blocks and SE blocks to improve learning performance and emphasize a relationship between channels. Hereinafter, the operation process of the waveform detection model according to one embodiment of the invention will be discussed in detail.

According to one embodiment of the invention, a waveform detection model $F_{seg}$ is intended to generate a semantic segmentation map ($S \in \mathbb{R}^{L \times C}$, where L=signal length, C=number of classes) from an input signal I(i.e., an ECG signal) ($I \in \mathbb{R}^{L}$). According to one embodiment of the invention, each encoding block included in the waveform detection model $F_{seg}$ may consist of a single CBR block ($F_{CBR}$: $\mathbb{R}^{L \times C} \rightarrow \mathbb{R}^{L \times C'}$) and four residual blocks ($F_{Res}$: $\mathbb{R}^{L \times C'} \rightarrow \mathbb{R}^{L \times C'}$), and a feature F ($F \in \mathbb{R}^{L \times C'}$) may be derived from a feature I by two successively connected CBR blocks ($F_{CBR1}$: $\mathbb{R}^{L \times C'} \rightarrow \mathbb{R}^{L \times C'}$, $F_{CBR2}$: $\mathbb{R}^{L \times C'} \rightarrow \mathbb{R}^{L \times C'}$) in each residual block. Further, according to one embodiment of the invention, an SE block arranged at the end of the two CBR blocks may derive a feature F LAP by performing a squeeze operation on the feature F using global average pooling (GAP) (wherein the squeeze operation is $$F_{GAP} = \frac{1}{L} \sum_{l=1}^{L} F(l, c)).$$

Furthermore, according to one embodiment of the invention, the SE block may perform an excitation operation using two fully-connected (FC) layers $$\left( FC_1 : \mathbb{R}^{l \times C'} \rightarrow \mathbb{R}^{\frac{l \times C'}{r}}, FC_2 : \mathbb{R}^{\frac{l \times C'}{r}} \rightarrow \mathbb{R}^{l \times C'} \right)$$

with a reduction ratio r being applied to the feature $F_{GAP}$, thereby deriving a channel excitation z (wherein the excitation operation is $z = \sigma(FC_2(\delta(FC_1(F_{GAP})))) \in \mathbb{R}^{1 \times C'}$, where $\sigma$=sigmoid activation function, $\delta$=ReLU activation function). According to one embodiment of the invention, the channel excitation z may be applied to an input feature $F_{in}$($F_{in} \in \mathbb{R}^{L \times C'}$) of each encoding block, resulting in an output feature Font of each encoding block being equal to $F_{out}$==I+z*$F_{in}$. According to one embodiment of the invention, the output feature of each encoding block may be passed to a decoding block corresponding to the encoding block in a skip-connection manner, and the decoding block may concatenate the feature passed in the skip-connection manner with a feature upsampled in a previous decoding block. According to one embodiment of the invention, the concatenated features may be passed through the CBR block and SE block in the decoding block, and the semantic segmentation map may be generated as the output from the last decoding block is passed through a convolution layer.

Through this process, the first detection unit 210 according to one embodiment of the invention may detect a QRS waveform (which may include a point $QRS_{on}$ where the QRS waveform begins and a point $QRS_{off}$ where the QRS waveform ends) in an ECG signal using a waveform detection model, and may further detect (or classify) a class of a cardiac event capable of being derived from the QRS waveform (e.g., normal sinus rhythm (NSR), ventricular premature contraction (VSP), or atrial premature contraction (APC)) (wherein the cardiac event is not necessarily limited to the above examples).

Next, the second detection unit 220 according to one embodiment of the invention may detect a unique R-peak in the QRS waveform detected in the ECG signal using a regression model.

Figure 4:
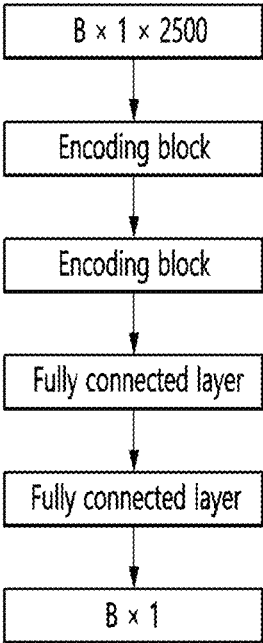
FIG. 4 shows the structure of a regression model according to one embodiment of the invention.

Here, the regression model according to one embodiment of the invention may include a plurality of encoding blocks formed in the same structure as the encoding blocks included in the above-described waveform detection model, and a plurality of FC layers. Specifically, referring to FIG. 4, the regression model according to one embodiment of the invention may be formed in a structure in which a plurality of encoding blocks (specifically, two encoding blocks) are successively connected, and a plurality of FC layers (specifically, two FC layers) are successively connected at the end of the plurality of successively connected encoding blocks. According to one embodiment of the invention, the plurality of FC layers may be intended for regression of a location of an R-peak in the QRS waveform. Meanwhile, according to one embodiment of the invention, an activation function applied to the last connected FC layer of the plurality of successively connected FC layers may differ from an activation function applied to the other FC layers (i.e., FC layers other than the last connected FC layer of the plurality of successively connected FC layers). Specifically, according to one embodiment of the invention, an ReLU activation function may be applied to the FC layers other than the last connected FC layer of the plurality of successively connected FC layers, whereas a sigmoid activation function may be applied to the last connected FC layer of the plurality of successively connected FC layers. Hereinafter, the operation process of the regression model according to one embodiment of the invention will be discussed in detail.

First, according to one embodiment of the invention, the QRS waveform detected by the waveform detection model may be resampled to a predetermined length $L_{reg}$ (e.g., $L_{reg}$=32) before being inputted to a regression model $F_{reg}$ (wherein rescaling may be performed on the QRS waveform along with the resampling). Meanwhile, according to one embodiment of the invention, the resampling process is not necessarily required and may be replaced (or eliminated) by using an adaptive pooling layer for generating an output of a fixed size. Then, according to one embodiment of the invention, the regression model $F_{reg}$ may determine (or predict) a normalized location $R_{norm}$ (a value between 0 and 1) of an R-peak ($F_{reg}$: $\mathbb{R}^{L_{qrs}} \rightarrow [0, 1]$) for the resampled data. Then, according to one embodiment of the invention, the regression model F reg may transform the normalized location $R_{norm}$ of the R-peak determined as above into a physical location $R_{samp}$ in the QRS waveform (specifically, linear transformation according to the equation $$R_{samp} = R_{norm} \times (QRS_{off} - QRS_{on}) + QRS_{on})$$

Figure 5:
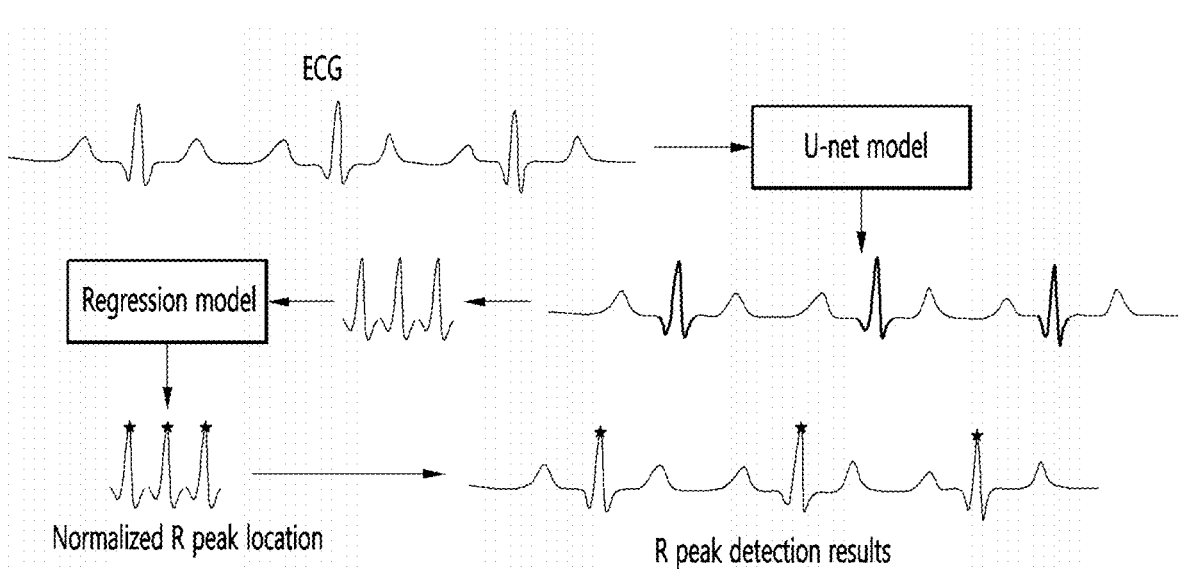
FIG. 5 schematically shows the overall process of detecting an R-peak in an ECG signal by an ECG signal processing system according to one embodiment of the invention.
Figure 6A:
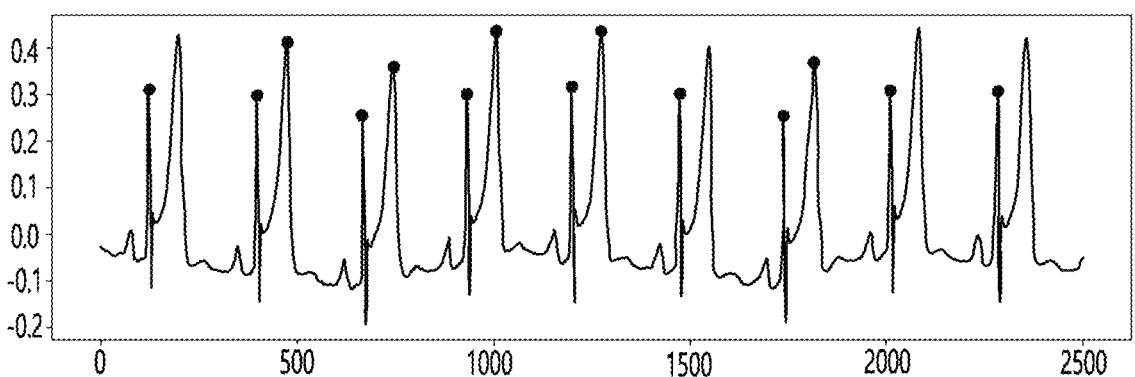
FIG. 6A shows the result of detecting an R-peak in an ECG signal using a general CNN-based model.
Figure 6B:
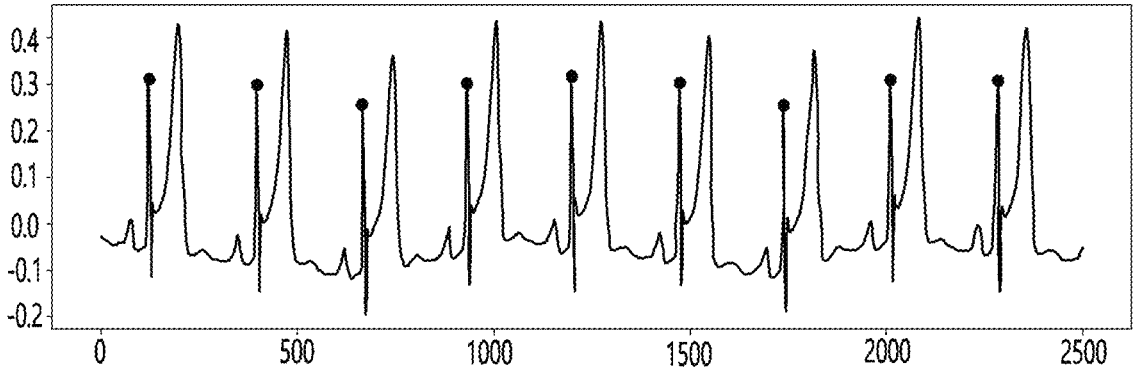
FIG. 6B shows the result of detecting an R-peak in an ECG signal by an ECG signal processing system according to one embodiment of the invention.

Through this process, the second detection unit 220 according to one embodiment of the invention may further perform a regression analysis on the output of the waveform detection model to detect a unique R-peak in a single QRS waveform (i.e., a two-step process) (FIG. 5 schematically shows the overall process according to one embodiment of the invention). Specifically, referring to FIG. 6, when detecting an R-peak in an ECG signal using only a general CNN-based model (specifically, a typical U-Net model), there is a tendency to detect both a true R-peak and a false positive R-peak (e.g., a T-wave may be detected as an R-peak when the T-wave is higher than the R-peak), resulting in a problem of detecting multiple R-peaks in a single QRS waveform (see FIG. 6A). However, when a regression analysis is further performed on the output of the CNN-based model (specifically, the waveform detection model) according to one embodiment of the invention, it is possible to detect a unique R-peak in a single QRS waveform (see FIG. 6B).

Further, when a regression analysis is further performed on the output of the CNN-based model (specifically, the waveform detection model) according to one embodiment of the invention, it is possible to detect a unique R-peak robustly and reliably over a long period of ECG signal measurements.

Next, the communication unit 230 according to one embodiment of the invention may function to enable data transmission/reception from/to the first detection unit 210 and the second detection unit 220.

Lastly, the control unit 240 according to one embodiment of the invention may function to control data flow among the first detection unit 210, the second detection unit 220, and the communication unit 230. That is, the control unit 240 according to the invention may control data flow into/out of the ECG signal processing system 200 or data flow among the respective components of the ECG signal processing system 200, such that the first detection unit 210, the second detection unit 220, and the communication unit 230 may carry out their particular functions, respectively.

The embodiments according to the invention as described above may be implemented in the form of program instructions that can be executed by various computer components, and may be stored on a computer-readable recording medium. The computer-readable recording medium may include program instructions, data files, and data structures, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler, but also high-level language codes that can be executed by a computer using an interpreter. The above hardware devices may be changed to one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

DESCRIPTION OF REFERENCE NUMERALS

100: communication network
200: ECG signal processing system
210: first detection unit
220: second detection unit
230: communication unit
240: control unit
300: device

What is claimed is:

1. A method performed in a system for detecting and classifying a beat in an electrocardiogram (ECG) signal, the system comprising one or more processors and the method comprising the steps of:

(a) by the one or more processors, detecting a QRS waveform in an ECG signal using a waveform detection model, and detecting a class of a cardiac event capable of being derived from the QRS waveform; and (b) by the one or more processors, detecting a unique R-peak in the QRS waveform using a regression model, wherein the waveform detection model is formed in a structure in which a plurality of encoding blocks and a plurality of decoding blocks are successively connected, wherein the plurality of encoding blocks include a CBR block and a plurality of residual blocks, the plurality of residual blocks being successively connected at an end of the CBR block, and wherein the plurality of decoding blocks include a CBR block and a squeeze-and-excitation (SE) block, the SE block being successively connected at an end of the CBR block.

2. The method of claim 1, wherein the waveform detection model is a model for performing semantic segmentation on the ECG signal.

3. The method of claim 1, wherein the regression model includes a plurality of encoding blocks formed in the same structure as encoding blocks included in the waveform detection model, and a plurality of fully connected (FC) layers.

4. The method of claim 1, wherein in step (b), a normalized location of an R-peak is determined for data obtained by resampling the QRS waveform to a predetermined length, and the normalized location of the R-peak is transformed into a physical location in the QRS waveform.

5. A non-transitory computer-readable recording medium having stored thereon a computer program for executing the method of claim 1.

6. A system for detecting and classifying a beat in an ECG signal, the system comprising one or more processors configured to:

detect a QRS waveform in an ECG signal using a waveform detection model, and detect a class of a cardiac event capable of being derived from the QRS waveform; and detect a unique R-peak in the QRS waveform using a regression model, wherein the waveform detection model is formed in a structure in which a plurality of encoding blocks and a plurality of decoding blocks are successively connected, wherein the plurality of encoding blocks include a CBR block and a plurality of residual blocks, the plurality of residual blocks being successively connected at an end of the CBR block, and wherein the plurality of decoding blocks include a CBR block and a squeeze-and-excitation (SE) block, the SE block being successively connected at an end of the CBR block.

7. The system of claim 6, wherein the waveform detection model is a model for performing semantic segmentation on the ECG signal.

8. The system of claim 6, wherein the regression model includes a plurality of encoding blocks formed in the same structure as encoding blocks included in the waveform detection model, and a plurality of fully connected (FC) layers.

9. The system of claim 6, wherein the one or more processors are configured to determine a normalized location of an R-peak for data obtained by resampling the QRS waveform to a predetermined length, and transform the normalized location of the R-peak into a physical location in the QRS waveform.

\*   \*   \*   \*   \*